US 12,417,536 B2

United States Patent
Chen et al.

(10) Patent No.: US 12,417,536 B2
(45) Date of Patent: Sep. 16, 2025

(54) AUTOMATED DETECTION SYSTEM FOR ACUTE ISCHEMIC STROKE

(71) Applicants: National Yang Ming Chiao Tung University, Hsinchu (TW); Kaohsiung Chang Gung Memorial Hospital, Kaohsiung (TW)

(72) Inventors: Yong-Sheng Chen, Taipei (TW); Wei-Che Lin, Kaohsiung (TW); Shih-Yen Lin, Huatan Township (TW); Hsiang-Chun Yang, Keelung (TW); Yu-Lin Yeh, New Taipei (TW); Evelyne Calista, Bekasi (ID); Pi-Ling Chiang, Kaohsiung (TW)

(73) Assignees: NATIONAL YANG MING CHIAO TUNG UNIVERSITY, Hsinchu (TW); KAOHSIUNG CHANG GUNG MEMORIAL HOSPITAL, Kaohsiung (TW)

( * ) Notice: Subject to any disclaimer, the term of this patent is extended or adjusted under 35 U.S.C. 154(b) by 342 days.

(21) Appl. No.: 18/209,830

(22) Filed: Jun. 14, 2023

(65) Prior Publication Data
US 2024/0312014 A1   Sep. 19, 2024

(30) Foreign Application Priority Data
Mar. 14, 2023   (TW) .................................. 112109331

(51) Int. Cl.
*G06T 7/00*   (2017.01)
*G06T 7/11*   (2017.01)
(Continued)

(52) U.S. Cl.
CPC .............. *G06T 7/0014* (2013.01); *G06T 7/11* (2017.01); *G06T 7/174* (2017.01); *G06V 10/245* (2022.01);
(Continued)

(58) Field of Classification Search
USPC .................................................. 382/131, 155
See application file for complete search history.

(56) References Cited

U.S. PATENT DOCUMENTS 10,163,040 B2 *  12/2018  Poole .......................... G06T 7/68
10,898,152 B1 *  1/2021   Kim ........................... G06T 7/11
(Continued)

FOREIGN PATENT DOCUMENTS

TW            202038252 A     10/2020

OTHER PUBLICATIONS

Aktar et al., "A Radiomics-Based Machine Learning Approach to Assess Collateral Circulation in Ischemic Stroke on Non-contrast Computed Tomography", in Multimodal Learning for Clinical Decision Support and Clinical Image-Based Procedures, 2020, Springer, p. 24-33.2.

(Continued)

*Primary Examiner* — Ishrat I Sherali
(74) *Attorney, Agent, or Firm* — Birch, Stewart, Kolasch & Birch, LLP

(57) ABSTRACT

In an automated detection system for acute ischemic stroke, a preprocessor performs registration on a whole-brain image and a standard-brain spatial template to extract individual brain region masks from the whole-brain image. A deep learning encoder performs feature extraction on the whole-brain image and the individual brain region masks, thereby converting the whole-brain image into 2D whole-brain slice images. A first processor maps the individual brain masks onto the whole-brain slice images for registration, thereby generating sets of brain region slice images. A second processor computes the stroke-related weight values of the slice images of each of the sets of brain region slice images and sums the weight values to obtain the characteristic value of each brain region. A disparity-aware classifier determines (Continued)

whether any brain region has acute ischemic stroke according to the characteristic value of each brain region.

8 Claims, 4 Drawing Sheets

(51) Int. Cl.
| | |
|---|---|
| *G06T 7/174* | (2017.01) |
| *G06V 10/24* | (2022.01) |
| *G06V 10/42* | (2022.01) |
| *G06V 10/764* | (2022.01) |
| *G06V 10/82* | (2022.01) |
| *G16H 30/40* | (2018.01) |
| *G16H 50/20* | (2018.01) |

(52) U.S. Cl.
CPC ............ *G06V 10/42* (2022.01); *G06V 10/764* (2022.01); *G06V 10/82* (2022.01); *G16H 30/40* (2018.01); *G16H 50/20* (2018.01); *G06T 2207/10081* (2013.01); *G06T 2207/20084* (2013.01); *G06T 2207/30016* (2013.01); *G06T 2207/30104* (2013.01); *G06V 2201/031* (2022.01)

(56) References Cited

U.S. PATENT DOCUMENTS

| | | | |
|---|---|---|---|
| 10,902,596 B2* | 1/2021 | Greveson | A61B 6/5205 |
| 11,200,664 B2* | 12/2021 | Yuh | A61B 6/501 |
| 11,315,263 B2* | 4/2022 | Wang | G06T 7/33 |
| 11,967,079 B1* | 4/2024 | Kumar | G06T 7/0012 |
| 2017/0140551 A1* | 5/2017 | Bauer | G06T 7/0012 |
| 2024/0006056 A1* | 1/2024 | Yu | G16H 30/40 |

OTHER PUBLICATIONS

Do et al., "Automatic Assessment of Aspects Using Diffusion-Weighted Imaging in Acute Ischemic Stroke Using Recurrent Residual Convolutional Neural Network", Diagnostics, 2020, vol. 10, No. 803, p. 1-12.

Khanh et al., "Assessment of Aspects from CT Scans using Deep Learning", Journal of Korea Multimedia Society, 2019, vol. 22, No. 5, p. 573-579.

Kniep et al., "Posterior circulation stroke: machine learning based detection of early ischemic changes in acute non contrast CT scans", Journal of neurology, 2020, vol. 267, p. 2632-2641.

Kuang et al., "Automated Aspects on noncontrast CT scans in patients with acute ischemic stroke using machine learning", American Journal of Neuroradiology, 2019, vol. 40, No. 1, p. 33-38.

Kuang et al., "Automated stroke lesion segmentation in non-contrast CT scans using dense multi-path contextual generative adversarial network", Physics in Medicine & Biology, 2020, vol. 65, 215013, total 15 pages.

Kuang et al., "EIS-Net: Segmenting Early Infarct and scoring Aspects Simultaneously on Non-contrast CT of Patients with Acute Ischemic Stroke", Medical Image Analysis, 2021, vol. 70, 101984, total 13 pages.

Takahashi et al., "Computerized identification of early ischemic changes in acute stroke in noncontrast CT using deep learning", in Medical Imaging 2019: Computer-Aided Diagnosis, 2019, International Society for Optics and Photonics, total 7 pages.

Clérigues et al., "Acute ischemic stroke lesion core segmentation in CT perfusion images using fully convolutional neural networks," Computers in Biology and Medicine, vol. 115, 2019 (Available online Oct. 9, 2019) 103487, pp. 1-7.

Taiwanese Office Action and Search Report for Taiwanese Application No. 112109331, dated Oct. 13, 2023, with an English translation.

* cited by examiner

AUTOMATED DETECTION SYSTEM FOR ACUTE ISCHEMIC STROKE

This application claims priority for TW patent application 112109331 filed on Mar. 14, 2023, the content of which is incorporated by reference in its entirely.

BACKGROUND OF THE INVENTION

Field of the Invention

The present invention relates to an automated detection system for medical images, particularly to an automated detection system for acute ischemic stroke.

Description of the Related Art

Non-contrast computed tomography (NCCT) is the most commonly used medical imaging technology to estimate the severity of acute ischemic stroke (AIS). In clinical application, the Alberta stroke program early CT score (ASPECTS) is the most important and widely used quantitative scoring system in the first-line decision-making of evaluating treatment options. This system involves assessing ischemic changes on computed tomography images of ten key regions supplied by the cerebral artery, including the caudate nucleus, putamen, internal capsule, insular cortex, and M1-M6 cortices. The ASPECTS has been proven to be a reliable biochemical marker for assessment and prognosis of AIS.

However, AIS detection using NCCT is often limited by its low sensitivity, because the brightness changes of AIS-related images are very subtle and difficult to identify. Therefore, the accurate assessment of ASPECTS usually requires years of experience of well-trained radiologists, and the assessment of different physicians will also be affected by their subjective determination. Furthermore, ASPECTS assessment by visual inspection is a time-consuming process. Identifying the imaging features of early AIS is critical for diagnosis because even a delay of a few minutes can lead to the death of neuronal cells. Early arterial recanalization and reperfusion may rescue hypoxic brain tissue and improve neurological functions. Therefore, reducing the time required for deciding the treatment option is critical to improving the viability of brain tissue. The development of a fast and accurate automatic AIS detection algorithm can serve as an effective tool for first-line clinicians to accelerate the treatment-deciding process, thereby leading to better prognosis.

To overcome the abovementioned problems, the present invention provides an automated detection system for acute ischemic stroke, so as to solve the afore-mentioned problems of the prior art and satisfy requirements in the future.

SUMMARY OF THE INVENTION

The primary objective of the present invention is to provide an automated detection system for acute ischemic stroke, which employs a dihedral group deep learning encoder to perform feature extraction on a whole-brain image and individual brain region masks to significantly reduce the number of model parameters and prevent from overfitting.

Another objective of the present invention is to provide an automated detection system for acute ischemic stroke, which effectively integrates stroke-related information in all slice images based on an attention mechanism.

Further objective of the present invention is to provide an automated detection system for acute ischemic stroke, wherein a disparity-aware classifier can consider both the features of a given region as well as the features of a region on the opposite side of the given region for stroke prediction.

In order to achieve the foregoing objectives, the present invention provides an automated detection system for acute ischemic stroke, which includes a preprocessor, a deep learning encoder, a first processor, a second processor, and a disparity-aware classifier. The preprocessor is configured to perform registration on a whole-brain image and a standard-brain spatial template to extract individual brain region masks from the whole-brain image. The individual brain region masks form a three-dimensional (3D) brain region mask. The deep learning encoder is coupled to the preprocessor and configured to perform feature extraction on the whole-brain image and the individual brain region masks, thereby converting the whole-brain image into a plurality of two-dimensional (2D) whole-brain slice images and identifying the bounding boxes of brain regions of each of the individual brain masks. The first processor is coupled to the deep learning encoder and configured to map the individual brain masks onto the whole-brain slice images for registration. The first processor is configured to divide the plurality of two-dimensional whole-brain slice images into the sets of brain region slice images based on the bounding boxes of the brain regions. Each of the sets of brain region slice images includes the slice images of a single brain region. The second processor is coupled to the first processor and configured to compute the stroke-related weight values of the slice images of each of the sets of brain region slice images. The second processor is configured to sum the weight values to obtain a characteristic value of each of the brain regions. The disparity-aware classifier is coupled to the second processor and configured to determine whether any brain region has acute ischemic stroke according to the characteristic value of each of the brain regions.

In an embodiment of the present invention, the whole-brain image is a non-contrast computed tomography (NCCT) image.

In an embodiment of the present invention, the whole-brain image is a three-dimensional image composed of the plurality of 2D whole-brain slice images.

In an embodiment of the present invention, the deep learning encoder is a two-dimensional (2D) convolutional neural network encoder. In an embodiment of the present invention, the sizes of the plurality of 2D whole-brain slice images generated by the deep learning encoder are equal to those of the individual brain masks. The number of the plurality of 2D whole-brain slice images generated by the deep learning encoder is equal to that of the individual brain masks.

In an embodiment of the present invention, the first processor includes an adaptive bounding volume unit, an adaptive max pooling unit, and a soft masking unit. The adaptive bounding volume unit is configured to divide the plurality of 2D whole-brain slice images into the sets of brain region slice images. The adaptive max pooling unit is coupled to the adaptive bounding volume unit and configured to down-sample the sets of brain region slice images. The soft masking unit is coupled to the adaptive max pooling unit and configured to perform element multiplication on the sets of brain region slice images down-sampled to generate a three-dimensional characteristic image of each brain region. The three-dimensional characteristic image is composed of the set of two-dimensional brain region slice images.

In an embodiment of the present invention, the second processor is configured to compute weight values of each of the sets of brain region slice images based on an attention mechanism.

In an embodiment of the present invention, the disparity-aware classifier is configured to compare the characteristic values of the brain regions of relative areas of a left brain and a right brain. When a difference value between the characteristic values of the brain regions of relative areas of a left brain and a right brain is greater than a given value, the disparity-aware classifier determines occurrence of acute ischemic stroke.

Below, the embodiments are described in detail in cooperation with the drawings to make easily understood the technical contents, characteristics and accomplishments of the present invention.

DETAILED DESCRIPTION OF THE INVENTION

The technical solutions in the embodiments of the present invention will be clearly and completely described below with reference to the drawings in the embodiments of the present invention. Obviously, the described embodiments are part of the embodiments of the present invention, not all of the embodiments. Based on the embodiments of the present invention, all other embodiments obtained by those skilled in the art without making inventive efforts should be included within the scope of the present invention.

It should be understood that, when used in this specification and the scope of the claims, the terms "comprising" and "including" refer to the presence of a stated feature, whole, step, operation, element, and/or component, but does not exclude the presence or addition of one or more other features, wholes, steps, operations, elements, components and/or combinations of these.

It should also be understood that the terms used in the specification of the present invention is only used to describe particular embodiments but not intended to limit the present invention. As used in this specification and the claims, the singular forms "a," "an," and "the" are intended to include the plural forms unless the context clearly dictates otherwise.

It should further be understood that the terms "and/or" used in the specification and the claims refer to any and all possible combinations of one or more of the associated listed items, and include these combinations.

Figure 1:
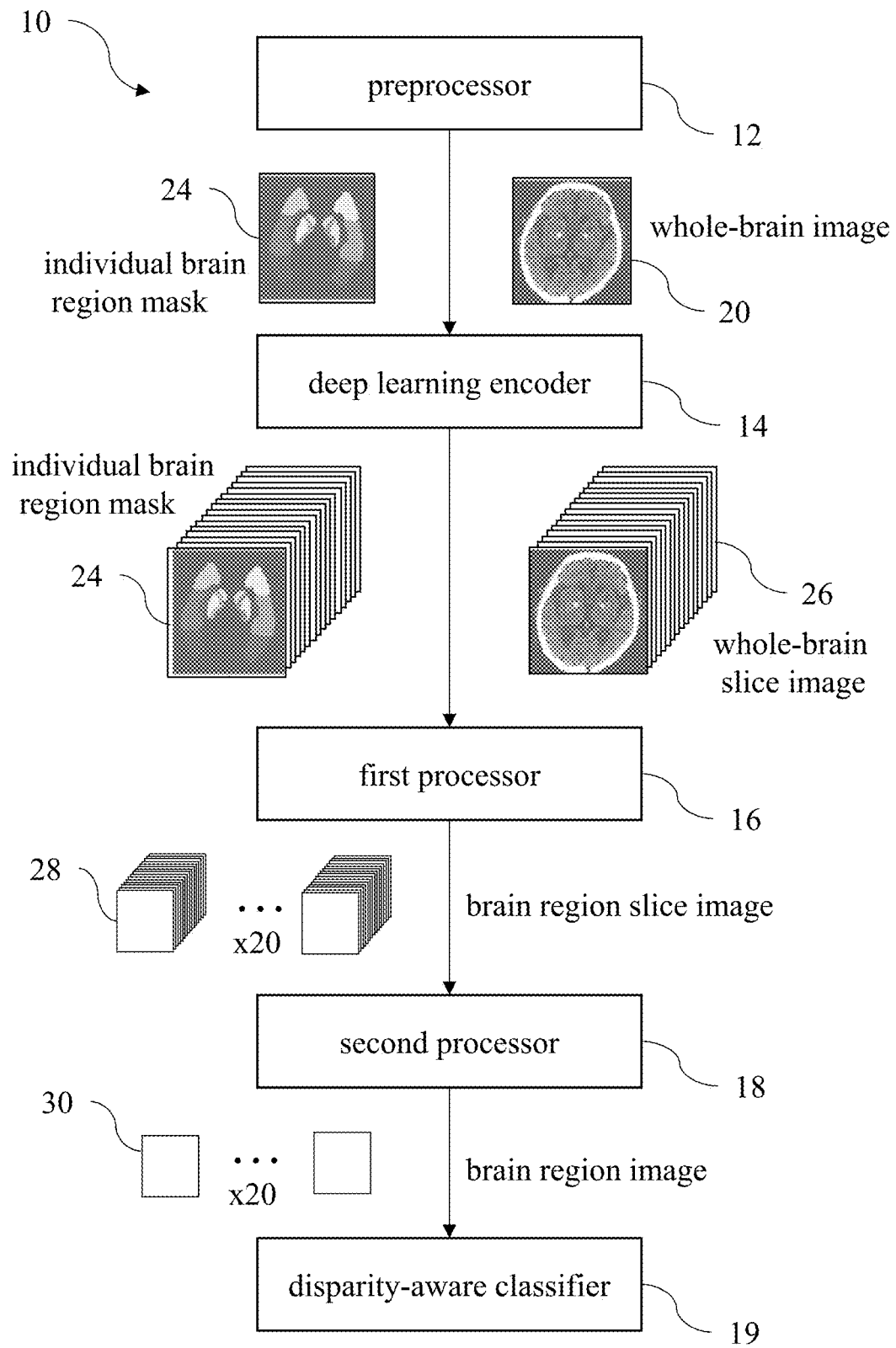
FIG. 1 is a schematic diagram illustrating an automated detection system for acute ischemic stroke according to an embodiment of the present invention.

The present invention provides an automated detection system for acute ischemic stroke. Please refer to FIG. 1. FIG. 1 is a schematic diagram illustrating an automated detection system 10 for acute ischemic stroke according to an embodiment of the present invention. The automated detection system 10 for acute ischemic stroke includes a preprocessor 12, a deep learning encoder 14, a first processor 16, a second processor 18, and a disparity-aware classifier 19. The preprocessor 12 is coupled to the deep learning encoder 14. The deep learning encoder 14 is coupled to the first processor 16. The first processor 16 is coupled to the second processor 18. The second processor 18 is coupled to the disparity-aware classifier 19.

Figure 2:
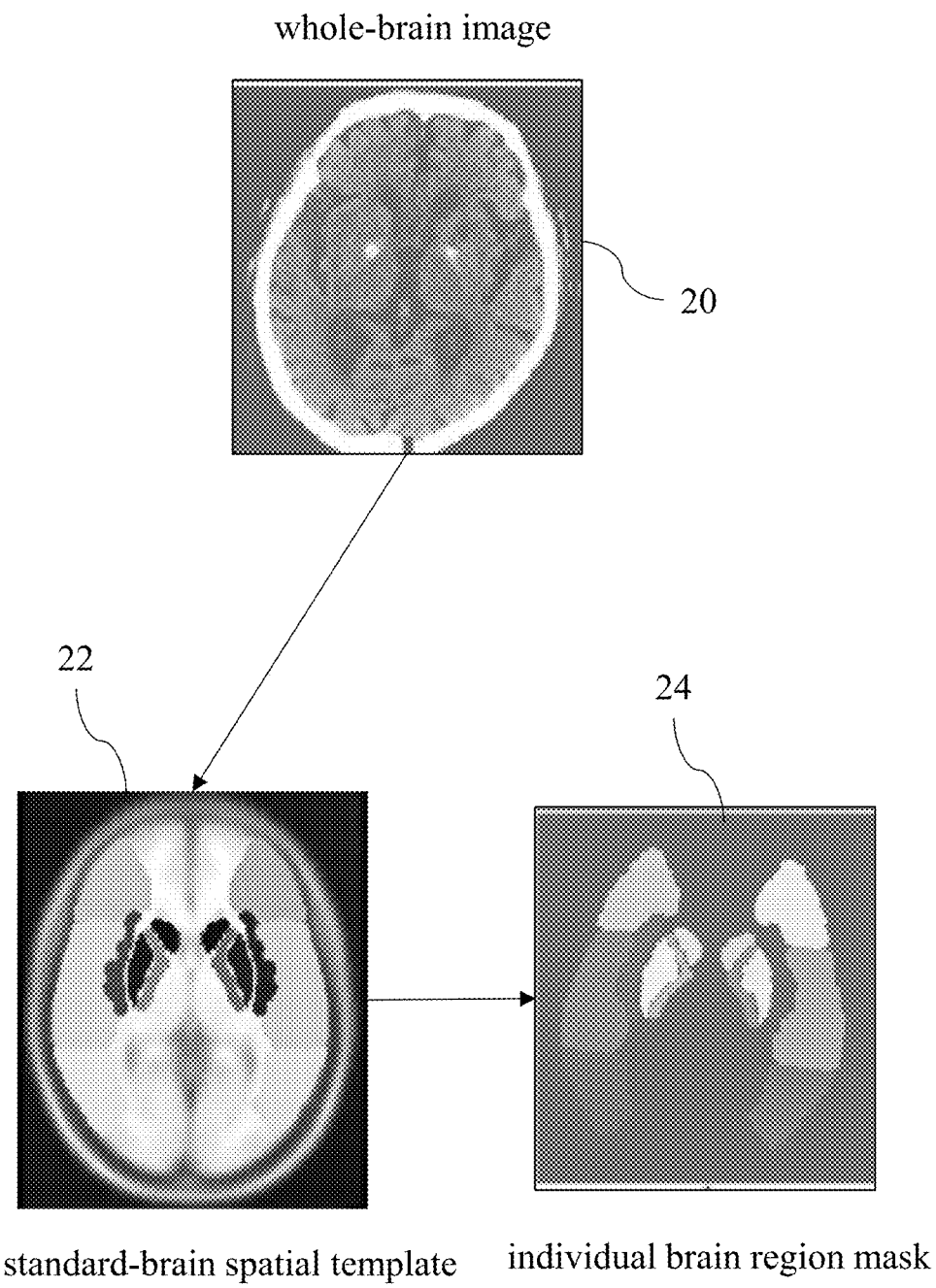
FIG. 2 is a schematic diagram illustrating an automated detection system for acute ischemic stroke with a preprocessor for extracting individual brain region masks according to an embodiment of the present invention.

The preprocessor 12 receive a whole-brain image 20 and performs registration on the whole-brain image 20 to generate individual brain region masks 24. The whole-brain image 20 is a non-contrast computed tomography (NCCT) image, which is a three-dimensional (3D) image. Please refer to FIG. 2. FIG. 2 is a schematic diagram illustrating a preprocessor 12 for extracting individual brain region masks 24 according to an embodiment of the present invention. The preprocessor 12 performs registration on the whole-brain image 20 and a standard-brain spatial template 22. The standard-brain spatial template 22 shows an upright standard brain space, which has been divided into multiple brain regions. In general, the standard brain space is divided into 20 brain regions, wherein a right brain and a left brain are symmetric to each other. Thus, each of the right brain and the left brain has 10 brain regions. The preprocessor 12 performs registration on the whole-brain image 20 and the standard-brain spatial template 22 to extract individual brain region masks 24 from the whole-brain image 20. For example, the individual brain region masks 24 have 20 brain regions. Since the brain space is three-dimensional, all brain regions will not be included in any brain section at the same time. Therefore, the individual brain region masks 24 can form a three-dimensional individual brain region mask corresponding to the shape of the user's brain space. The individual brain region masks 24 divides multiple brain regions corresponding to the individual's whole-brain image 20, but the boundaries of the brain regions of the individual brain region mask 24 are not apparent. This is because the whole-brain image 20 does not show an upright brain space. The whole-brain image 20 cannot align with the standard-brain spatial template 22 completely.

The deep learning encoder 14 is configured to clearly identify the boundaries of brain regions. The deep learning encoder 14 includes a first encoder (not illustrated) and a second encoder (not illustrated). The first encoder performs feature extraction on the whole-brain image 20, and converts the three-dimensional whole-brain image 20 into a plurality of two-dimensional whole-brain slice images 26. In other words, the whole-brain image 20 is composed of a plurality of whole brain slice images. The second encoder performs feature extraction on the individual brain region masks 24, converts the individual brain region masks 24 into two-dimensional individual brain region masks, and identifies the bounding boxes of multiple brain regions of the two-dimensional individual brain region masks 24, so that the 20 brain regions are clearly divided. The sizes of the plurality of 2D whole-brain slice images 26 generated by the deep learning encoder 14 are equal to those of the two-dimensional individual brain masks 24. The number of the plurality of 2D whole-brain slice images 26 generated by the deep learning encoder 14 is equal to that of the two-dimensional individual brain masks 26. In one embodiment, the first encoder of the deep learning encoder 14 is a dihedral group convolutional neural network (CNN) encoder, and the second encoder is implemented with matched average pooling.

The first processor 16 is configured to map the individual brain masks 24 onto the whole-brain slice images 26 for registration. Then, the first processor 16 divides the plurality of two-dimensional whole-brain slice images 26 into sets of brain region slice images 28 based on the bounding boxes of the brain regions. Each of the sets of brain region slice images 20 includes the slice images of a single brain region. Assume that there are 100 whole-brain slice images 26 and that there are 20 brain regions. There are 20 sets of brain region slice images 28. Each set of brain region slice images 28 includes 100 slice images of a single brain region.

Specifically, the first processor 16 may include an adaptive bounding volume unit (not illustrated), an adaptive max pooling unit (not illustrated), and a soft masking unit (not illustrated). The adaptive bounding volume unit is configured to divide the plurality of 2D whole-brain slice images 26 into the sets of brain region slice images 28. The adaptive max pooling unit is coupled to the adaptive bounding volume unit and configured to down-sample the sets of brain region slice images 28 to reduce the sizes of the sets of brain region slice images 28.

For example, the sizes of the sets of brain region slice images 28 are reduced to 4*4 images. The soft masking unit is coupled to the adaptive max pooling unit and configured to perform element multiplication on the sets of brain region slice images 28 down-sampled, such that sets of two-dimensional brain slice images 28 are superimposed together to generate the three-dimensional characteristic image of each brain region.

The second processor 18 receives the three-dimensional characteristic image by superimposing the sets of two-dimensional brain slice images 28 and computes the stroke-related weight values of the slice images of each of the sets of brain region slice images. The second processor 18 sums the weight values to obtain a characteristic value of each of the brain regions. At this time, only one brain region image 30 is left for each brain region, and the characteristic value is assigned to the brain region image 30. Since the whole brain can be divided into 20 brain regions, there are 20 characteristic values in total. In one embodiment, the second processor 18 computes the weight values of each of the sets of brain region slice images 28 based on an attention mechanism.

Figure 3:
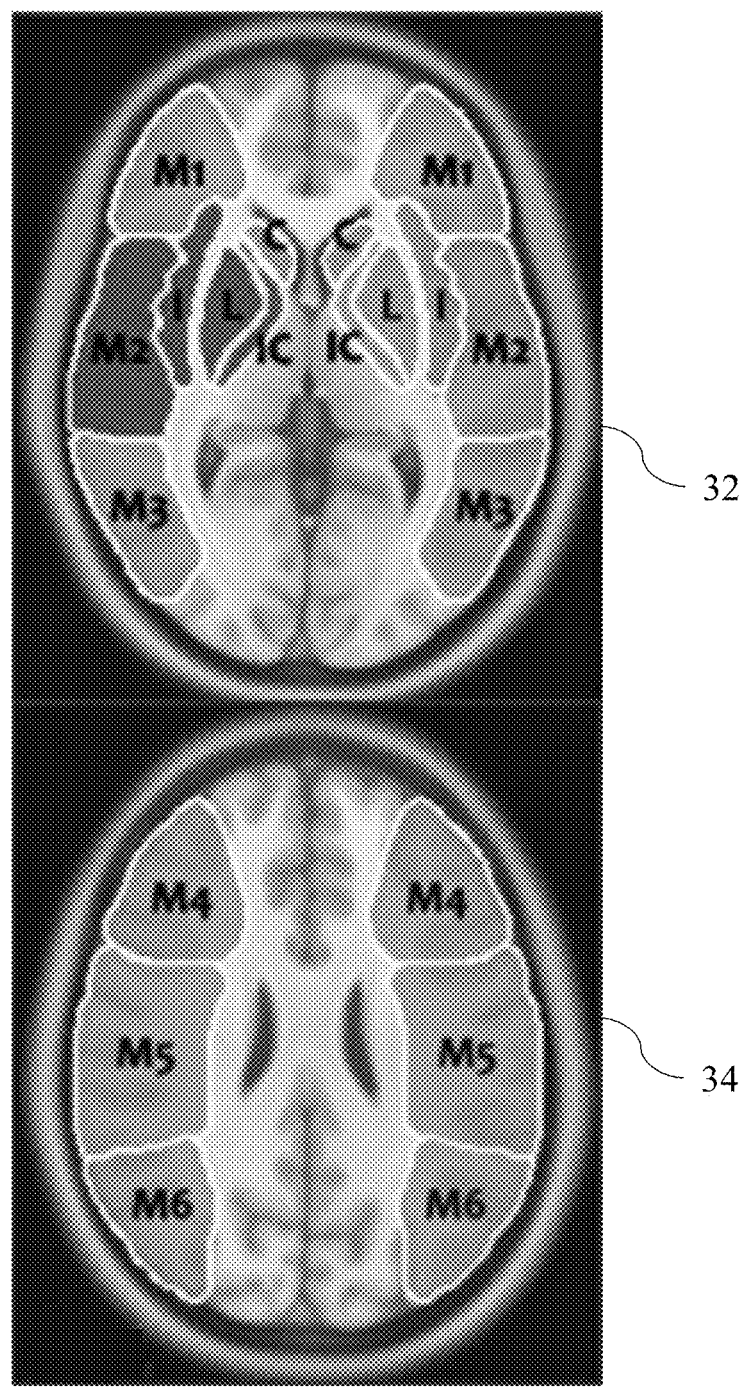
FIG. 3 is a schematic diagram illustrating a disparity-aware classifier that shows images for acute ischemic stroke according to an embodiment of the present invention.

The disparity-aware classifier 19 determines whether any brain region has acute ischemic stroke according to the characteristic value of each of the brain regions. The disparity-aware classifier 19 compares the characteristic values of the brain regions of relative areas of a left brain and a right brain. When a difference value between the characteristic values of the brain regions of relative areas of a left brain and a right brain is greater than a given value, the disparity-aware classifier determines the occurrence of acute ischemic stroke. As illustrated FIG. 3, the first group of symmetric brain regions is called M1, the second group of symmetric brain regions is called M2, and so on. Not all brain regions are included in the first whole-brain slice image 32, and some brain regions not shown are included in the second whole-brain slice image 34. Normal brain regions are colored light gray. After comparing the relative left and right brain regions, the disparity-aware classifier 19 determines that the characteristic value of the M2 brain region of the left brain relative to the characteristic value of the M2 brain region of the right brain is abnormal. Thus, the M2 brain region of the left brain is marked in dark gray, which represents the M2 brain region of the left brain has acute ischemic stroke.

Figure 4:
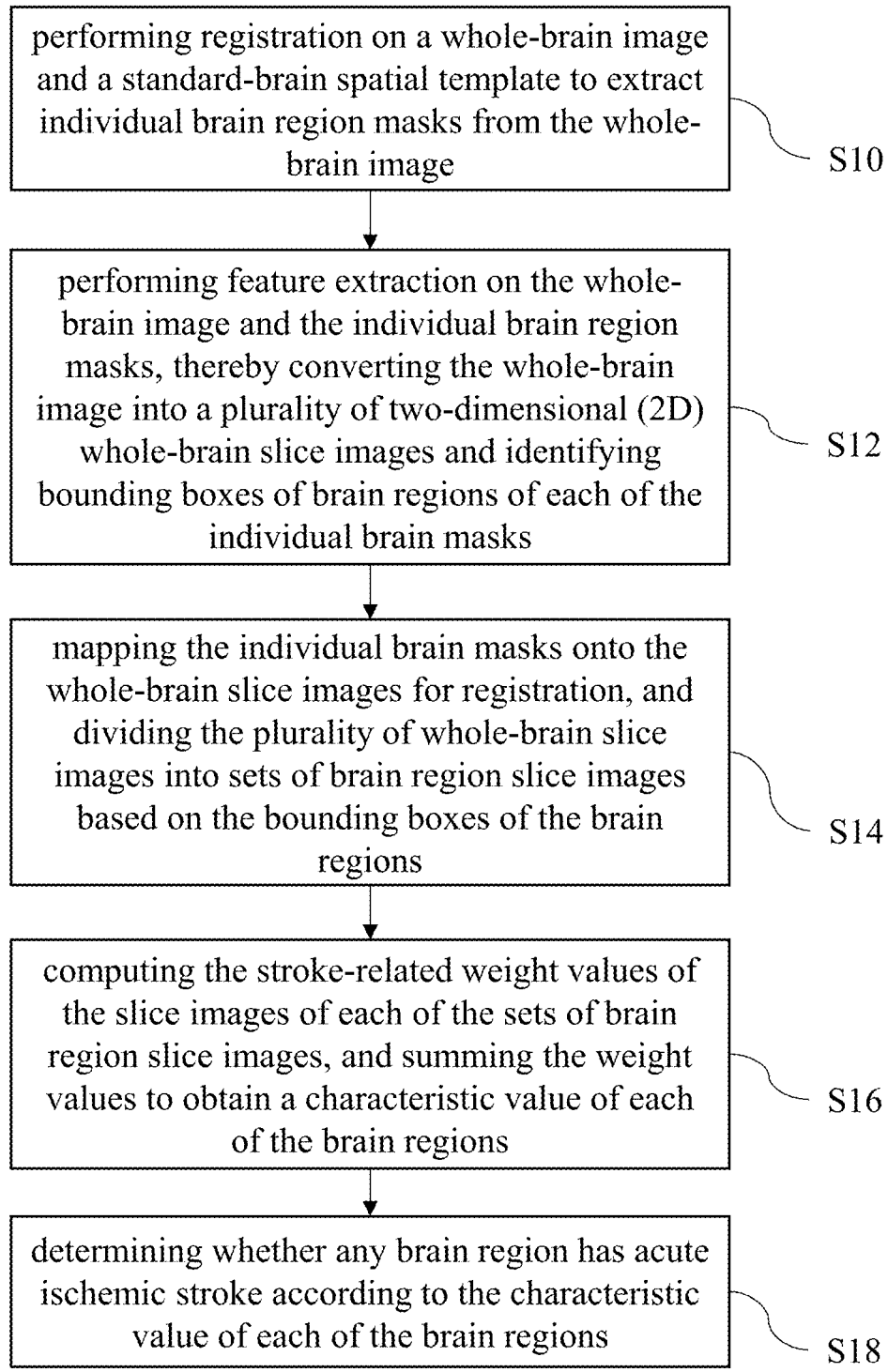
FIG. 4 is a flowchart of operating an automated detection system for acute ischemic stroke according to an embodiment of the present invention.

Please refer to FIG. 1 and FIG. 4. FIG. 4 is a flowchart of operating an automated detection system 10 for acute ischemic stroke according to an embodiment of the present invention. In Step S10, the preprocessor 12 performs registration on a whole-brain image 20 and a standard-brain spatial template 22 to extract individual brain region masks 24 from the whole-brain image 20. In Step S12, the deep learning encoder 14 performs feature extraction on the whole-brain image 20 and the individual brain region masks 24, thereby converting the whole-brain image 20 into a plurality of two-dimensional (2D) whole-brain slice images 26 and identifying the bounding boxes of brain regions of each of the individual brain masks 24. In Step S14, the first processor 16 maps the individual brain masks 24 onto the whole-brain slice images 26 for registration, and divides the plurality of whole-brain slice images 26 into sets of brain region slice images 28 based on the bounding boxes of the brain regions. In Step S16, the second processor 18 computes the stroke-related weight values of the slice images of each of the sets of brain region slice images 28, and sums the weight values to obtain a characteristic value of each of the brain regions. In Step S18, the disparity-aware classifier 19 determines whether any brain region has acute ischemic stroke according to the characteristic value of each of the brain regions.

In conclusion, the automated detection system for acute ischemic stroke of the present invention uses non-contrast computed tomography (NCCT) for feature extraction, comparison, and interpretation. Compared with the low sensitivity of the NCCT Alberta stroke program early CT score (ASPECTS) of visual detection, the present invention significantly improves the detection performance of acute ischemic stroke to serve as a reliable reference for clinical diagnosis, reduces pressure on radiologists, and makes faster ASPECTS assessments for faster treatment decision-making.

The embodiments described above are only to exemplify the present invention but not to limit the scope of the present invention. Therefore, any equivalent modification or variation according to the shapes, structures, features, or spirit disclosed by the present invention is to be also included within the scope of the present invention.

What is claimed is:

1. An automated detection system for acute ischemic stroke comprising:
a preprocessor configured to perform registration on a whole-brain image and a standard-brain spatial template to extract individual brain region masks from the whole-brain image, wherein the individual brain region masks form a three-dimensional (3D) brain region mask;
a deep learning encoder coupled to the preprocessor and configured to perform feature extraction on the whole-brain image and the individual brain region masks, thereby converting the whole-brain image into a plurality of two-dimensional (2D) whole-brain slice images and identifying bounding boxes of brain regions of each of the individual brain masks;
a first processor coupled to the deep learning encoder and configured to map the individual brain masks onto the whole-brain slice images for registration, wherein the first processor is configured to divide the plurality of two-dimensional whole-brain slice images into sets of brain region slice images based on the bounding boxes of the brain regions, and each of the sets of brain region slice images comprises slice images of a single brain region;

a second processor coupled to the first processor and configured to compute stroke-related weight values of the slice images of each of the sets of brain region slice images, wherein the second processor is configured to sum the weight values to obtain a characteristic value of each of the brain regions; and a disparity-aware classifier coupled to the second processor and configured to determine whether any one of the brain regions has acute ischemic stroke according to the characteristic value of each of the brain regions.

2. The automated detection system for acute ischemic stroke according to claim 1, wherein the whole-brain image is a non-contrast computed tomography (NCCT) image.

3. The automated detection system for acute ischemic stroke according to claim 1, wherein the whole-brain image is a three-dimensional image composed of the plurality of 2D whole-brain slice images.

4. The automated detection system for acute ischemic stroke according to claim 1, wherein the deep learning encoder is a two-dimensional (2D) convolutional neural network encoder.

5. The automated detection system for acute ischemic stroke according to claim 1, wherein sizes of the plurality of 2D whole-brain slice images generated by the deep learning encoder are equal to those of the individual brain masks, and number of the plurality of 2D whole-brain slice images generated by the deep learning encoder is equal to that of the individual brain masks.

6. The automated detection system for acute ischemic stroke according to claim 1, wherein the first processor comprises:
    an adaptive bounding volume unit configured to divide the plurality of 2D whole-brain slice images into the sets of brain region slice images;
    an adaptive max pooling unit coupled to the adaptive bounding volume unit and configured to down-sample the sets of brain region slice images; and
    a soft masking unit coupled to the adaptive max pooling unit and configured to perform element multiplication on the sets of brain region slice images down-sampled to generate a three-dimensional characteristic image of each of the brain regions, wherein the three-dimensional characteristic image is composed of the set of two-dimensional brain region slice images.

7. The automated detection system for acute ischemic stroke according to claim 1, wherein the second processor is configured to compute the weight values of each of the sets of brain region slice images based on an attention mechanism.

8. The automated detection system for acute ischemic stroke according to claim 1, wherein the disparity-aware classifier is configured to compare characteristic values of the brain regions of relative areas of a left brain and a right brain, and when a difference value between the characteristic values is greater than a given value, the disparity-aware classifier determines occurrence of acute ischemic stroke.

* * * * *